(12) United States Patent
Crooks et al.

(10) Patent No.: US 7,077,939 B1
(45) Date of Patent: Jul. 18, 2006

(54) METHOD AND APPARATUS FOR NANOPARTICLE TRANSPORT AND DETECTION

(75) Inventors: Richard M. Crooks, College Station, TX (US); Li Sun, College Station, TX (US)

(73) Assignee: The Texas A&M University System, College Station, TX (US)

(*) Notice: Subject to any disclaimer, the term of this patent is extended or adjusted under 35 U.S.C. 154(b) by 261 days.

(21) Appl. No.: 10/173,905

(22) Filed: Jun. 17, 2002

Related U.S. Application Data

(60) Provisional application No. 60/299,399, filed on Jun. 18, 2001.

(51) Int. Cl.
 - *G01N 27/447* (2006.01)
 - *G01N 27/28* (2006.01)
 - *C12Q 1/68* (2006.01)
 - *B01D 61/00* (2006.01)
 - *F17D 1/00* (2006.01)

(52) U.S. Cl. .................. 204/450; 204/409; 422/50; 422/99; 210/500.23; 210/500.22; 137/1

(58) Field of Classification Search .............. 422/99, 422/100, 50, 68.1, 82.01, 83; 204/450, 451, 204/600, 601, 409, 603, 452; 137/1; 210/500.23, 210/500.22
See application file for complete search history.

(56) References Cited

U.S. PATENT DOCUMENTS

| 5,843,767 A | * | 12/1998 | Beattie ................ 435/287.1 |
|---|---|---|---|
| 6,589,682 B1 | * | 7/2003 | Fleckner et al. .......... 429/34 |
| 6,616,821 B1 | * | 9/2003 | Broadley et al. ........... 204/435 |
| 6,696,185 B1 | * | 2/2004 | Okamoto ................ 429/12 |

OTHER PUBLICATIONS

CAPLUS abstract of Rezania et al. ("Bioactivation of Metal Oxide Surfaces. 1. surface Characterization and Cell Response," Langmuir (1999), 15(20), 6931-6939).*
CAPLUS abstract of Puleo ("Immobilization of protein on silanized orthopedic biomaterials," Materials Research Society Symposium Proceedings (1994), 331(Biomaterials for Drug and Cell Delivery), 269-74).*
CAPLUS abstract of Butler (US 4006059).*
CAPLUS abstract of Patel et al. ("Printing patterns of biospecifically-adsorbed protein," journal of Biomaterials Science, Polyme Edition (2000), 11(3), 319-331).*
CAPLUS abstract of Dubrovsky ("Immobilization of protein monolayers on planar solid supports," Protein architeture (2000),2554, Editor(s): Lvov, Yuri; Moehwald, Helmuth. Publisher: Marcel Dekker, Inc. New York, N.Y.).*
Ajayan et al. (<< Aligned Carbon Nanotube Arrays Formed by Cutting a Polymer Resin-Nanotube Composite. >> Science, New Series, vol. 265, No. 5176 (Aug. 26, 1994), 1212-1214).*
R. W. DeBlois, C. P. Bean, J., "*Electrokinetic Measurements with Submicron Particles and Pores by the Resistive Pulse Technique*" Colloid Interface Sci. 61, pp. 323-335, Sep. 1977.

(Continued)

*Primary Examiner*—Alex Noguerola
(74) *Attorney, Agent, or Firm*—Baker Botts L.L.P.

(57) ABSTRACT

According to one embodiment an apparatus includes a membrane and at least a portion of a nanotube imbedded within the membrane. The portion of the nanotube imbedded within the membrane provides a conduit through the membrane.

26 Claims, 9 Drawing Sheets

OTHER PUBLICATIONS

M. R. Ghadiri, J. R. Granja, L. K. Buehler, "*Artificial Transmembrane Ion Channels from Self-assembling Peptide Nanotubes,*" Nature 369, pp. 301-304, May 26, 1994.

G. Widawski, M. Rawiso, B. Francois, "*Self-Organized Honeycomb Morphology Of Star-Polymer Polystyrene Films*", Nature 369, pp. 387-389, Jun. 2, 1994.

J. J. Kasianowicz, E. Brandin, D. Branton, D. Deamer, "*Characterization of Individual Polynucleotide Molecules Using a Membrane Channel,*" Proc. Natl. Acad. Sci. U.S.A. 93, pp. 13770-13773, Nov. 1996.

B. D. Bath, R. D. Lee, H. S. White, "*Imaging Molecular Transport in Porous Membranes, Observation and Analysis of Electroosmotic Flow in Individual Pores Using the Scanning Electrochemical Microscope,*" Anal. Chem. 70, pp. 1047-1058, Mar. 15, 1998.

L. Sun, R. M. Crooks, "*Fabrication and Characterization of Single Pores for Modeling Mass Transport Across Porous Membranes,*" Langmuir 15, pp. 738-741, Jan. 8, 1999.

L.-Q. Gu, O. Braha, S. Conlan, S. Cheley, H. Bayley, "*Stochasitc Sensing of Organic Analytes by a Pore-Forming Protein Containing a Molecular Adapter,*" Nature 398, pp. 686-690, Apr. 22, 1999.

L. Sun, R. M. Crooks, "*Single Carbon Nanotub Membranes: A Well-Defined Model for Studying Mass Transport through nanoporous Materials,*" J. Am. Chem. Soc. 122, pp. 12340-12345, Nov. 18, 2000.

* cited by examiner

METHOD AND APPARATUS FOR NANOPARTICLE TRANSPORT AND DETECTION

RELATED APPLICATIONS

This application claims the benefit under 35 U.S.C. §119 (e) of the filing date of U.S. Provisional Application Ser. No. 60/299,399, filed Jun. 18, 2001 entitled Fabrication and Application of Single-Nanopore Membranes.

GOVERNMENT RIGHTS

The work described in this patent application was developed under National Science Foundation grants CHE-9796203 and CHE-9818302 and Department of Energy contract No. DE-FG03-01ER15247. The U.S. Government may have certain rights in this patent application.

TECHNICAL FIELD OF THE INVENTION

This invention relates in general to nanoparticles, and more particularly to a method and apparatus for nanoparticle transport and detection.

BACKGROUND OF THE INVENTION

Transport in nanoporous media differs from ordinary transport in bulk media. Nanoporous material refers generally to material having one or more pores less than one micrometer in size. The differences arise largely because the interactions between the pore surface and the molecule being transported become increasingly important as the dimensions of the pore approach the size of the molecule.

Conventional nanopore models, such as dialysis membranes or polymeric woven-fiber membranes, contain a large array of pores with polydisperse structural parameters; that is, nanopores in these membranes exhibit a wide distribution in either shape, size, or surface chemistry. Quantitative data analysis for such models is difficult to implement because a complete description of a polydisperse structure is almost impossible without invoking many approximations and assumptions.

More recently, materials containing arrays of pores with one or more monodisperse structural parameters have been reported: for example, membranes derived from etched polycarbonate (Nucleopore) or porous alumina membranes and porous structures fabricated from monodisperse nanoscopic and mesoscopic objects. Membrane models containing monodisperse pore-arrays do have some drawbacks. First, it is difficult to ensure structural uniformity in arrays containing 10 or more pores (assuming a pore diameter of 100 nm and a sample area of 1 cm$^2$); the problem is exacerbated as the pore dimensions become very small. Second, under steady-state conditions, only a time-averaged transport rate can be determined because individual single-pore transport events cannot be temporally resolved from each other. Thus, statistical distribution in transport rate cannot be retrieved using an array-pore membrane model.

Single-pore membranes represent a new type of structural model for studying mass-transport kinetics. Since the number of variables required for complete structural description is less than for array-pore membranes, single-pore membranes are more useful for directly testing specific predictions of theory. Single-pore membranes allow measurement of the temporal response of a single pore, which is useful for obtaining stochastic information about transport parameters or for investigating time-dependent properties such as voltage- or chemically induced gating. Single nanopores consisting of membrane proteins have been studied previously. However, these protein channels are dynamically complex structures and may not be good models for testing existing theories.

One challenge often encountered when relying on single-pore membrane models for transport studies is that very few methods exist that allow convenient fabrication of single-pore membranes with pore dimensions on the nanometer scale. Current methods for producing single-pore membranes generally fall into two categories: the first includes methods based on optical or e-beam lithography, and the second includes the methods based on radiation damage (e.g., Nucleopore membranes track-etched by low density, high-energy fission fragments or inorganic membranes such as a sapphire membrane drilled by a focused laser beam).

SUMMARY

According to one embodiment of the present invention the apparatus includes a membrane and at least a portion of a nanotube imbedded within the membrane. The portion of the nanotube imbedded within the membrane provides a conduit through the membrane.

According to another embodiment of the invention, a method for delivering material to a desired location includes providing a nanotube holder between the material and the desired location. The nanotube holder has a portion of a nanotube disposed therein and provides a conduit through the nanotube holder. The method also includes forcing the material through the holder to the desired location by forcing the material through the nanotube.

Some embodiments of the present invention provide a number of technical advantages. For example, according to one embodiment of the present invention using a nanotube in combination with a membrane to produce a membrane having a single nanopore overcomes some of the disadvantages described above with previous single nanopore membranes. Membranes having a plurality of nanopores may also be produced in a similar fashion. Furthermore, some embodiments of the invention provide additional advantages. For example, the geometric and chemical properties of the resulting nanopore may be well-defined because of the characteristics of the nanotube. In particular, for a carbon nanotube, the pore diameter is usually uniform along the entire pore length and a set of nanoporous membranes of essentially identical diameter can be obtained if they are all derived from a common nanotube. This is a clear advantage over most lithographic methods in which very tight control over fabrication conditions is required to achieve identical replicates. Additionally, wall 14 of nanotube 10, in one embodiment, is an atomically smooth graphic sheet, which may be the best approximation of theoretical models that assumes a "structureless wall." Good approximation of the critical models allows for more accurate particle detection when membrane 16 is used in particle detection. Additionally, a single nanotube embedded within a highly stable polymeric matrix, in one embodiment, constitutes a good configuration for reducing interference due to leakage and Faradic currents because the polymer matrix is normally a good insulator for both electron and ion conduction. Many such nanopore membranes can be prepared rapidly due to the efficiency of certain manufacturing approaches, some of which are described below. This greatly enhances reproducibility and reduces sample preparation time, making the approach practical for routine studies.

Embodiments of the present invention may enjoy some, all, or none of these advantages. Other technical advantages are readily apparent to one skilled in the art from the following figures, the description, and the claims.

BRIEF DESCRIPTION OF THE DRAWINGS

Reference is made to the following description taken in conjunction with the accompanying drawings in which.

DETAILED DESCRIPTION OF EXAMPLE EMBODIMENTS OF THE INVENTION

Example embodiments of the invention are best understood by referring to FIGS. 1A through 6 of the drawings in which like numerals refer to like parts.

Figure 1A:
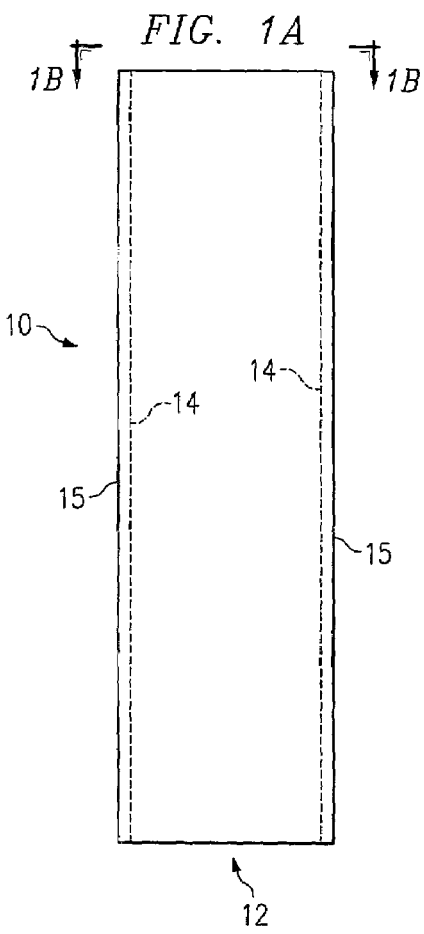
FIG. 1A shows an elevational view of a single nanotube.
Figure 1B:
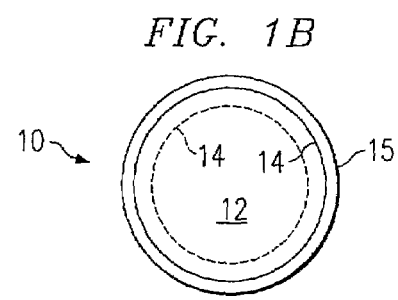
FIG. 1B is a plan view of the nanotube of FIG. 1A.
Figure 1C:
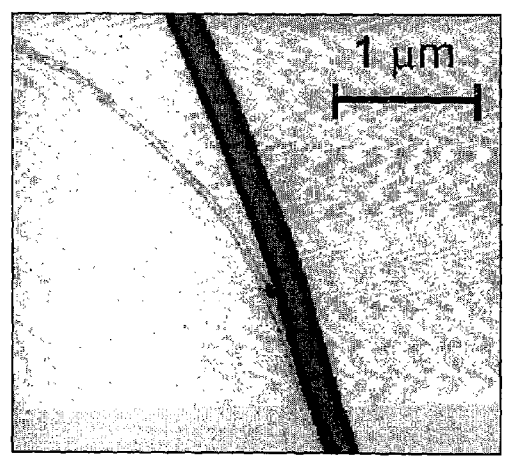
FIG. 1C is a photograph of a multi-wall carbon nanotube, as seen in a Transmission Electron Microscope (TEM) image.

FIG. 1A is a schematic diagram of a nanotube 10, and FIG. 1B is plan view of nanotube 10 along the lines 1-B of FIG. 1A. As illustrated in FIG. 1A, nanotube 10 is formed with a core section, or pore 12, surrounded by one or more walls 14. In some nanotubes, surrounding the one or more walls 14 is a coating 15. In one embodiment, coating 15 is an amorphous carbon layer; however, if a coating is utilized, any coating that facilitates the manipulation of the nanotube in the subsequent steps as illustrated in FIG. 3, may be used. For example, the coating may improve the visibility of the nanotube under an optical microscope, or improve the mechanical strength of the nanotube so that it will not break easily under mechanical stress that may result from handling or manipulation of the nanotube as illustrated in FIG. 3. The interior wall of some nanotubes may coated with a thin layer of chemical such as surfactant, polymer, or metal (not explicitly shown), which imparts the interior wall with one or more desired surface properties such as wettability, binding selectivity toward molecules present in pore 12, and net surface electric charge that can be either positive or negative. Wall 14 may be found from carbon, carbon in combination with other materials, or from non-carbon materials, including boron nitride, molybdenum disulfide, and other material that forms wrapped sheet or tubular structures which can exist as isolated tubes. FIG. 1C shows an image of a multi-walled nanotube coated with amorphous carbon.

Nanotubes are generally tubes having a very small diameter, less than one micrometer. They have been studied for applications in the following areas: (a) use of nanotubes as low-resistance electron conductors (Stefan F.; Poncharal, P.; Wang, Z. L.; de Heer, W. A. *Science* 1998, 280, 1744–1746), (b) use of nanotubes as components for building transistors (Wind, S. J.; Appenzeller, J.; Martel, R.; Derycke, V.; Avouris, Ph. *Appl. Phys. Lett.* 2002, 80, 3817–3819), (c) use of nanotubes as probe tips for scanning force microscopy (SFM) and scanning tunneling microscopy (STM) ([i] Wong, S. S.; Harper, J. D.; Peter T. Lansbury, J.; Lieber, C. M. *J. Am. Chem. Soc.* 1998, 120, 603–604. [ii] Dai, H.; Hafner, J. H.; Rinzler, A. G.; Colbert, D. T.; Smalley, R. E. *Nature* 1996, 384, 1476–150.), (d) use of nanotubes as field emission tips (Fan, S.; Chapline, M. G.; Franklin, N. R.; Tombler, T. W.; Cassell, A. M.; Dai, H. *Science* 1999, 283, 512–514.), and (e) use of nanotubes as media for hydrogen storage (Dillon, A. C.; Jones, K. M.; Bekkedahl, T. A.; Kiang, C. H.; Bethune, D. S.; Heben, M. J. *Science* 1997, 386, 377–379). Nanotubes suitable for use with the present invention include carbon nanotubes, nanotubes formed from a combination of carbon and other materials, and non-carbon nanotubes. Such nanotubes may be multi-walled, which means there are a plurality of wall layers surrounding core 12, or they may be single walled, as illustrated in FIG. 1A. The dotted lines in FIG. 1B represent an example of an additional wall 14 in a multi-walled nanotube.

One characteristic that makes a nanotube particularly suitable for detecting and transporting nanoparticles (small particles having a size less than about one micrometer) is the smoothness of the interior surface of wall 14; however if nanotube 10 were made without a particularly smooth wall 14, it could also be used according to the teachings of the invention, but would likely result in less desirable operation. According to one embodiment of the invention, nanotube 10 is produced such that its inner wall 14 is atomically smooth. Techniques for producing nanotubes are well known, and they can be roughly divided into three general classes. The first class of production technique is known as electric arc-discharge technique, which has been used in the following examples: (a) Iijima, S.; Ichihashi, T. *Nature* 1993, 363, 603–605; (b) Ajayan, P. M.; Lambert, J. M.; Bernier, P.; Barbedette, L.; Colliex, C.; Planeix, J. M. *Chem. Phys. Lett.* 1993, 215, 509–517; and (c) Kanai, M.; Koshio, A.; Shinohara, H.; Mieno, T.; Kasuya, A.; Ando, Y.; Zhao, X. *Appl. Phys. Lett.* 2001, 79, 2967–2969. The second type of technique for nanotube production uses laser ablation of a precursor target, and this technique has been used in the following examples: (a) Guo, T.; Nikolaev, P.; Thess, A.; Colbert, D. T.; Smalley, R. E. *Chem. Phys. Lett.* 1995, 243, 49–54; (b) Thess, A.; Lee, R.; Nikolaev, P.; Dai, H.; Petit, P.; Robert, J.; Xu, C.; Lee, Y. H.; Kim, S. G.; Rinzler, A. G.; Colbert, D. T.; Scuseria, G. E.; Tomanek, D.; Fischer, J. E.; Smalley, R. E. *Science* 1996, 273, 483–487; and (c) Lebedkin, S.; Schweiss, P.; Renker, B.; Malik, S.; Hennrich, F.; Neumaier, M.; Stoermer, C.; Kappes, M. M. *Carbon* 2002, 40, 417–423. The third type of nanotube synthesis involves the use of chemical vapor deposition: for example, (a) Tibbetts, G. G. *Carbon* 1992, 30, 399–406; (b) Ren, Z. F.; Huang, Z. P.; Xu, J. W.; Wang, J. H.; Bush, P.; Siegal, M. P.;

Provencio, P. N. *Science* 1998, 282, 1105–1107; (c) Fan, S.; Chapline, M. G.; Franklin, N. R.; Tombler, T. W.; Cassell, A. M.; Dai, H. *Science* 1999, 283, 512–514; (d) Nikolaev, P.; Bronikowski, M. J.; Bradley, R. K.; Rohmund, F.; Colbert, D. T.; Smith, K. A.; Smalley, R. E. *Chem. Phys. Lett.* 1999, 313, 91–97; (e) Ma, R.; Bando, Y.; Sato, T. *Chem. Phys. Lett.* 2001, 337, 61–64; and (f) Hsu, W. K.; Chang, B. H.; Zhu, Y. Q.; Han, W. Q.; Terrones, H.; Terrones, M.; Grobert, N.; Cheetham, A. K.; Kroto, H. W.; Walton, D. R. M. *J. Am. Chem. Soc.* 1998, 122, 10155–10158. Nanotubes are also commercially available from CarbolLex (University of Kentucky, Lexington, Ky. 40506), Applied Sciences (141 West Xenia Av., P.O. Box 579, Cedarville, Ohio 45314), and DEAL International (P.O. Box 20144, Rochester, N.Y. 14602).

Nanotubes are often produced to have a generally circular cross-section with core 12 also being generally circular, as illustrated in FIG. 1B; however, nanotubes suitable for use with the present invention could take any cross-sectional configuration that would allow a particle to flow through it. For example, the cross-section could be elliptical or irregularly shaped.

According to the teachings of the invention, a membrane 16A (FIG. 2A) may be formed with nanotube 10 disposed therein, thus providing a membrane having a single nanopore through which particles may flow. Alternatively a membrane 16B (FIG. 2B) having a nanopore may be formed by removing the nanotube from membrane 16A, resulting in a membrane with a single nanopore. Using a nanotube in combination with a membrane to produce a membrane having a single nanopore overcomes some of the disadvantages described above with previous single nanopore membranes. Membranes having a plurality of nanopores may also be produced in a similar fashion. Furthermore, some embodiments of the invention provide additional advantages. For example, the geometric and chemical properties of the resulting nanopore may be well-defined because of the characteristics of the nanotube. In particular, for a carbon nanotube, the pore diameter is usually uniform along the entire pore length and a set of nanoporous membranes of essentially identical diameter can be obtained if they are all derived from a common nanotube. This is a clear advantage over most lithographic methods in which very tight control over fabrication conditions is required to achieve identical replicates. Additionally, wall 14 of nanotube 10, in one embodiment, is an atomically smooth graphic sheet, which may be the best approximation of theoretical models that assumes a "structureless wall." Good approximation of the critical models allows for more accurate particle detection when membrane 16 is used in particle detection. Additionally, a single nanotube embedded within a highly stable polymeric matrix, in one embodiment, constitutes a good configuration for reducing interference due to leakage and Faradic currents because the polymer matrix is normally a good insulator for both electron and ion conduction. Many such nanopore membranes can be prepared rapidly due to the efficiency of certain manufacturing approaches, some of which are described below. This greatly enhances reproducibility and reduces sample preparation time, making the approach practical for routine studies.

Figure 2A:
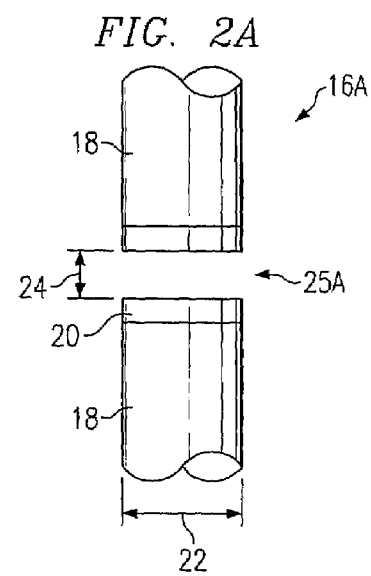
FIG. 2A is a schematic diagram of a nanopore membrane according to the teachings of the invention.

FIG. 2A illustrates a completed single nanopore membrane 16A according to the teachings of the invention. Single nanopore membrane 16A comprises a membrane 18 formed of a solid matrix and a portion 20 of nanotube 10 forming a nanopore 25A therethrough. As illustrated, both ends of nanotube portion 20 are open to surrounding media. Although the particular dimensions of single nanopore membrane 16 differ depending upon its intended application, generally, the height 22 of nanotube portion 20 is about five times the inside diameter 24 of nanopore 25A, or less. For nanotubes not having a true diameter, this guideline should be applied to an appropriate characteristic length, as determined by one skilled in the art. Membrane 18 may be formed from any liquid, gaseous, or plurality of particles that may be solidified in a configuration surrounding nanotube 10, including polymers and inorganic materials such as silica or silicon nitride.

Figure 2B:
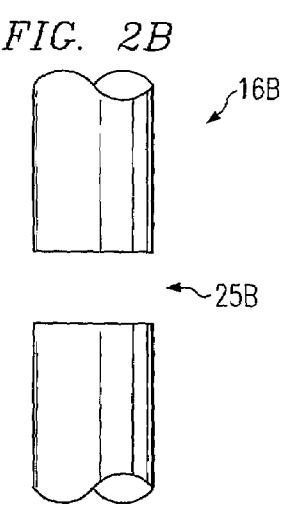
FIG. 2B is a schematic diagram of an alternative embodiment of a nanopore membrane according to the teachings of the invention.

FIG. 2B illustrates an alternative embodiment of a completed single nanopore membrane 16B according to the teachings of the invention. Nanopore membrane 16B is analogous to nanopore membrane 16A, except that nanotube portion 20 has been removed, leaving nanopore 25B. In this example, nanopore 25B is therefore slightly larger than nanopore 25A.

Nanopore membrane 16 (both membranes 16A and 16B) may be used for a plurality of purposes and particularly for detecting the movement of particles through nanopore 25 (either nanospore 25A or 25B) of nanotube portion 20, and thus may be used as a particle detector. Such detection is described in greater detail below in conjunction with FIGS. 5A through 5E. One example technique for constructing nanopore membrane 16A is described below with respect to FIGS. 3A through 3F, and one example technique for constructing nanopore membrane 16B is described below in conjunction with FIGS. 4A through 4F; however, other techniques may also be used to produce such nanopore membranes 16.

Figure 3A:
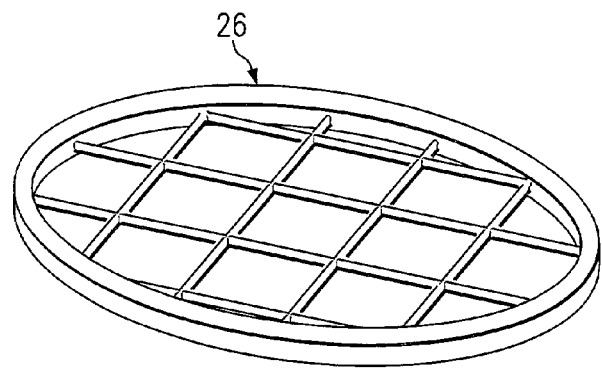
FIGS. 3A through 3F illustrates example acts associated with one embodiment of forming the nanopore membrane of FIG. 2A according to the teachings of the invention.
Figure 3B:
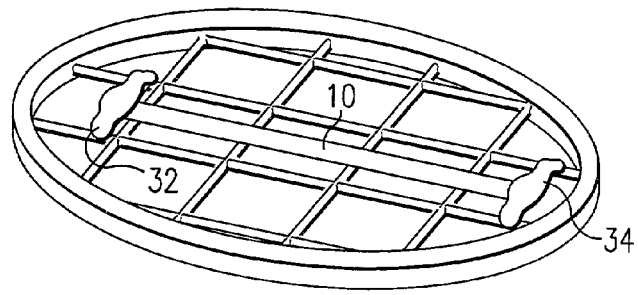

FIGS. 3A through 3F show example acts associated with one embodiment of forming single nanopore membrane 16A according to the teachings of the invention; however, other methods of fabricating single nanopore membrane 16A may be utilized. As illustrated in FIG. 3A a Transmission Electron Microscope (TEM) grid 26 is provided. Grid 26 is used in FIG. 3B to support nanotube 10 before a material 28 (FIG. 2D) is formed around nanotube 10. In FIG. 2B, a single carbon nanotube 10 may be removed from a raw mass (not explicitly shown) by using a tungsten tip (such as the one described in Melmed, A. J. *J. Vac. Sci. Technol.* B. 1991, 9, 601) precoated with an acrylic adhesive. The tungsten tip which is glued to one end of the nanotube 10 may then be manipulated with the aid of an x,y,z translation stage, such as Model 462 available from Newport of Irvine, Calif., to move it towards TEM grid 26. In this example, TEM grid 26 is a 200-mesh gold grid; however any suitable grid that can support nanotube 10 may be used.

The free end of the nanotube 10 is glued to grid 26, as illustrated in FIG. 2B. In one example embodiment the glue used is a heat-curable silver epoxy 32, such as H20S, available from Epoxy Technology, Billerica, Mass.; however, other epoxies and glues may be used. Nanotube 10 is stretched into a straight line while the other end of it is glued to grid 30 with the epoxy, as denoted by reference numeral 34. Application of the silver epoxy 32, 34 to grid 28 may be performed with a blunt W-tip under the control of another x,y,z translation stage, or other suitable technique. In particular embodiments, nanotube 10 is positioned across the centers of the grid openings in grid 30. At this stage in manufacture, nanotube 10 may be examined with the TEM to make sure that nanotube 10 is not filled with epoxy 32, 34 during the operation described in conjunction with FIG. 3B; FIG. 3C illustrates a TEM image showing such examination.

Figure 3D:
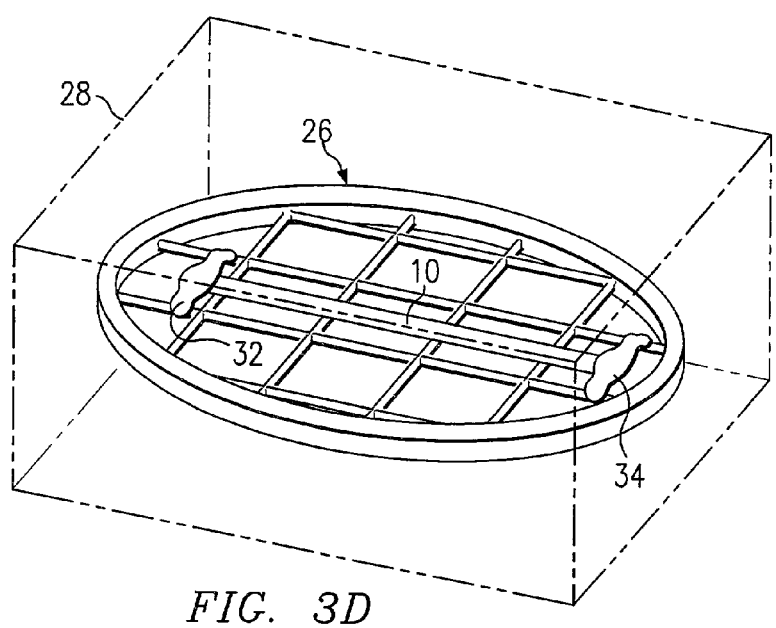
Figure 3C:
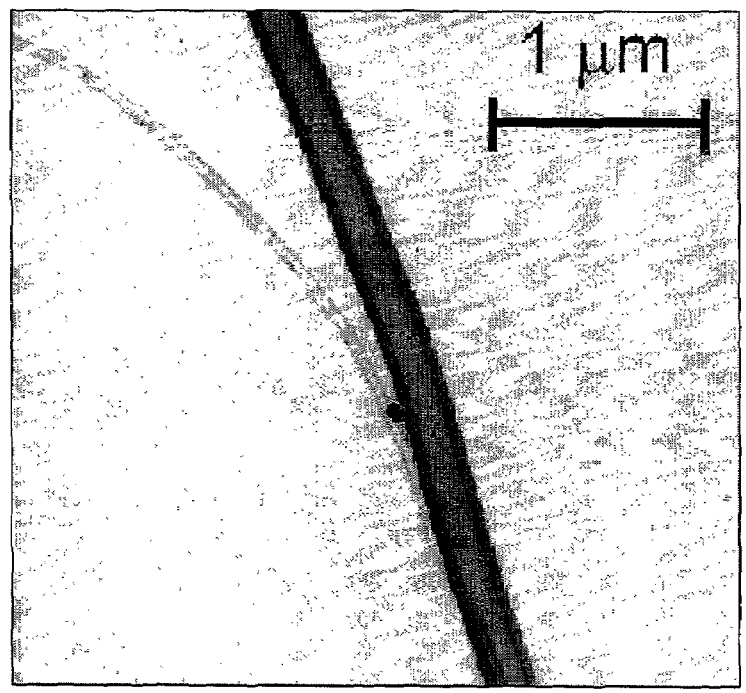
Figure 3F:
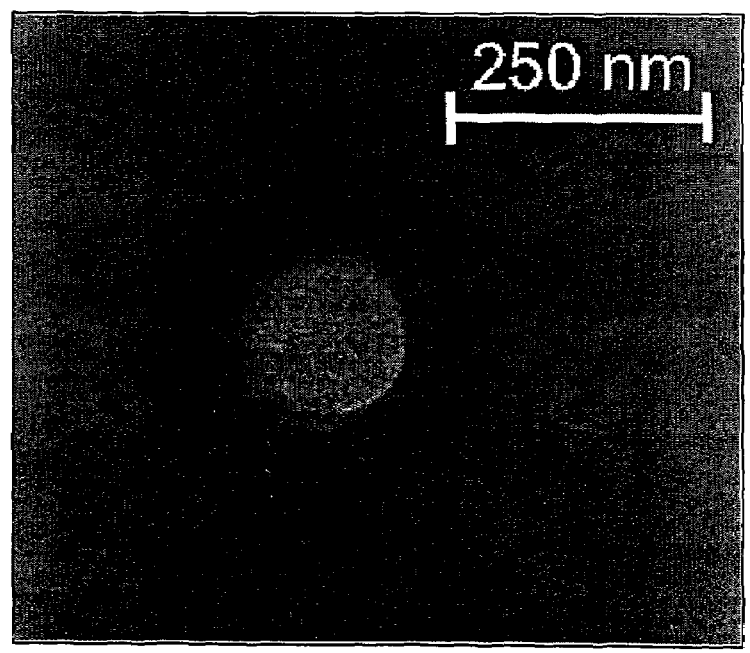
Figure 3E:
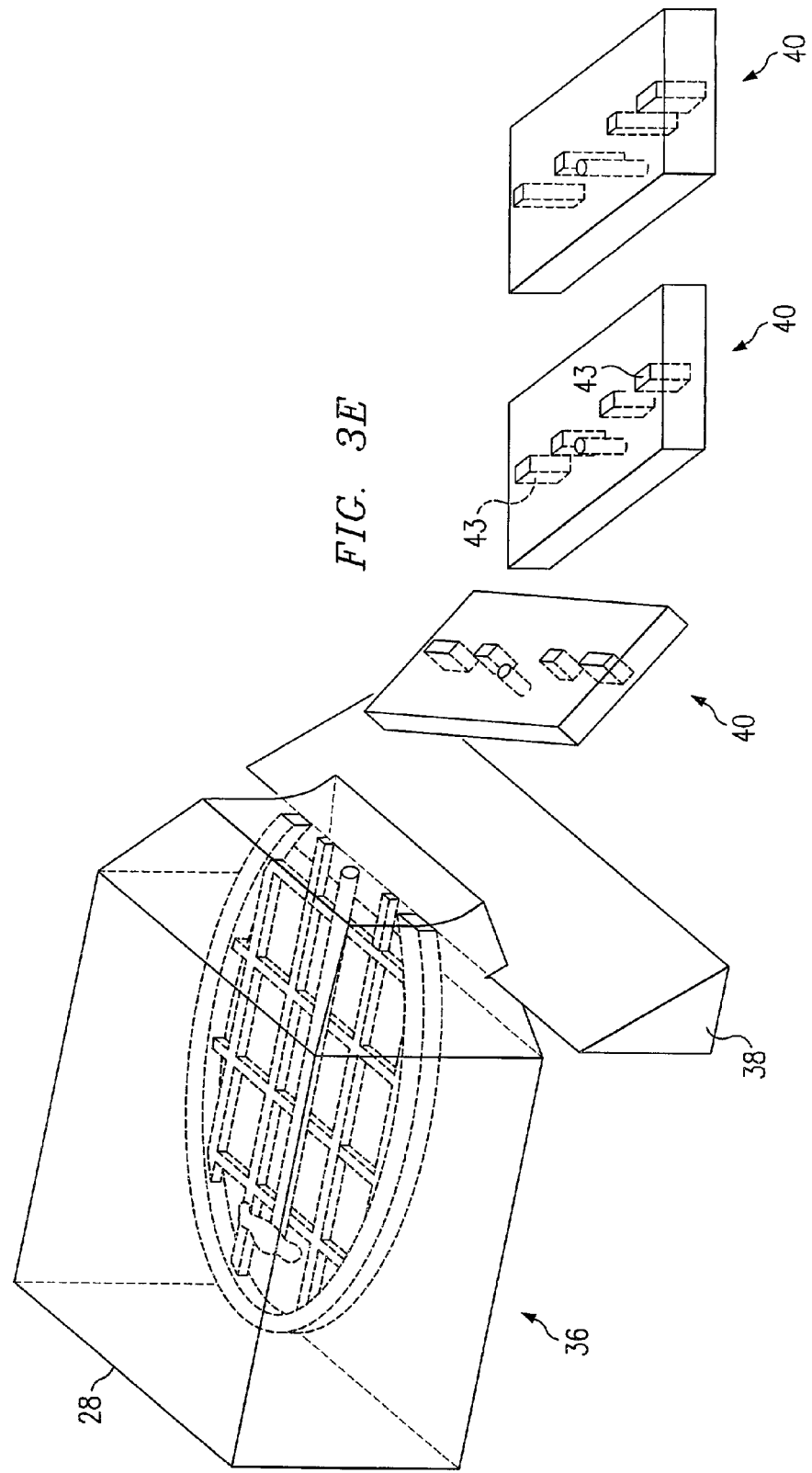

In FIG. 3D, the combination of grid 26 and nanotube 10 is positioned in a silicone mold, such as those available from Electron Microscopy Sciences, Ft. Washington, Pa.; however any mold that could hold a liquid or gas for solidification may be used. An imbedding epoxy, such as Epo-Fix available from Electron Microscopy Sciences, is poured into the mold and cured, in this example, at room temperature for over twenty-four hours; however, other materials that harden into solid state may also be used for forming material 28 together with other curing times and temperatures. This results in the structure shown in FIG. 2D, with material 28 surrounding both nanotube 10 and grid 26.

The resulting combination 36 illustrated in FIG. 2D may then be microtomed, as illustrated in FIG. 2E, to obtain a plurality of thin membranes 40, analogous to nanoporous membranes 16A, with very smooth surfaces. In one example, a diamond knife 36, such as model 6389LH, 45-degree included angle, 6-degree clearance angle, available from Microspace Star Technologies, Huntsville, Tex., may be used; however, any suitable knife, laser, or other device that may be used to section membranes 16A from combination 36 may be used. A representative section 40 may then be imaged again with the TEM to determine accurately the diameter of nanotube 10, as illustrated in a TEM image shown in FIG. 3F.

The grid bars of grid 26 appear as a linear set of regularly spaced dots 43 flanking the nanotube pore 12. These grid dots 43 are not a concern because they are located a large distance away from nanotube 10. This distance is much larger than the effective distance around nanotube pore 12 beyond which a section 40 is later attached onto a support structure, as illustrated in FIG. 5.

Figure 4A:
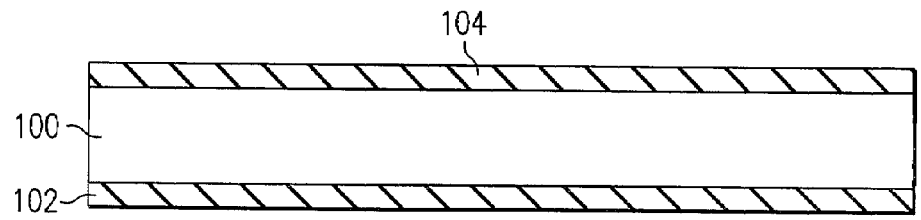
FIGS. 4A through 4F show example acts associated with one embodiment of forming the nanopore membrane of FIG. 2B according to the teachings of the invention.
Figure 4B:
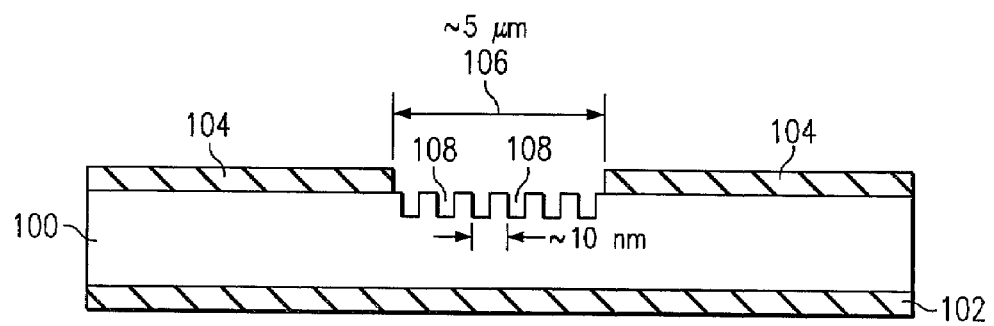

FIGS. 4A through 4F illustrate one example of the fabrication of nanopore membrane 16B; however, other methods of fabricating nanopore membrane 16B may be utilized. A silicon wafer 100 is coated on both sides with silicon nitride layers 102 and 104, as illustrated in FIG. 4A. A small window 106 of about five microns in diameter is then created on the smooth front surface 104 using standard optical lithography and followed by reactive ion etching, as illustrated in FIG. 4B. Nearly vertical arrays of holes 108 are then etched into the exposed silicon surface. An example procedure for this etching is described in *Thin Solid Films*, 1995, 255, 1–4 by Lehmann, V. The diameters of holes 108 depends on specific desired conditions, but holes 108 on the order of ten nanometers in diameter may be created.

Figure 4C:
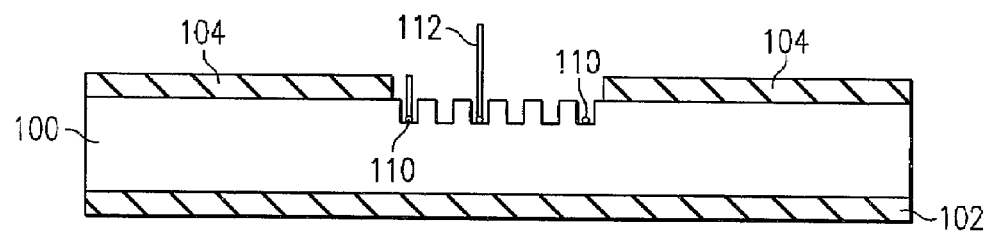
Figure 4D:
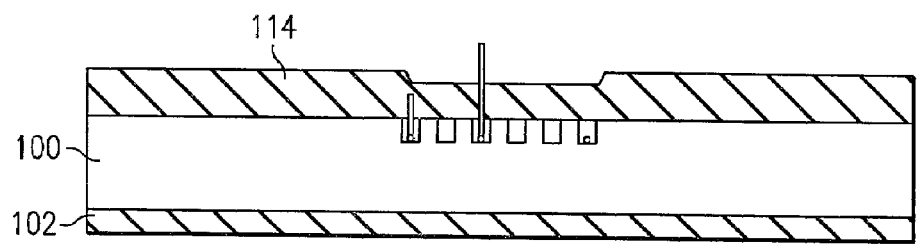
Figure 4E:
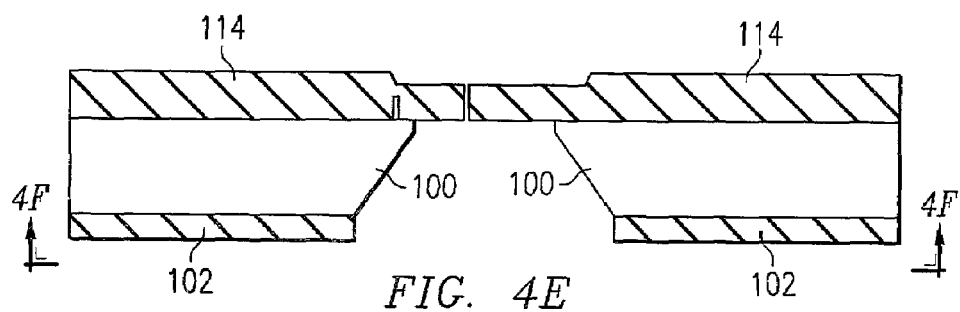
Figure 4F:
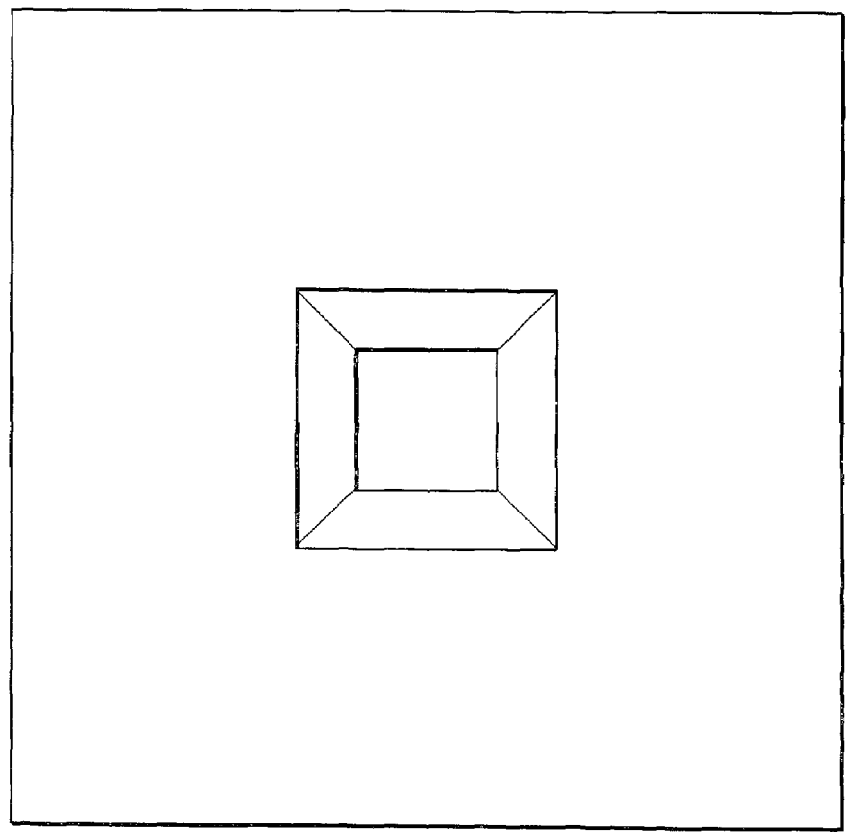

As shown in FIG. 4C, small iron particles 110 are then deposited inside holes 108 using an electrochemical procedure. One example of a procedure for such deposition is described in *Nature* 1999, 398, 761–762 by Hafner, J. H.; Cheung, C. O.; Lieber, C. M. Alternatively, colloidal iron particles or protein carriers containing a known amount of iron atoms may be introduced into holes 108 directly by simply soaking a silicon sample in a solution containing iron particles and subsequently drying off the solvent. The procedure for making the iron particles is described in *J. Phys. Chem. B* 2001, 105, 11424–11431, by Lee Y.; Kim, W.; Zhang, Y.; Rolandi, M.; Wang, D.; Dai, H. Carbon nanotubes 112 are grown using a chemical vapor deposition method in which iron particles 110 act as seed catalysts. Depending on the growth conditions, the average length of the carbon nanotubes can be controlled, and chemical vapor deposition is stopped when the length is larger than the expected thickness of a silicon nitride membrane, such as membrane 16B. A silicon nitride membrane 114 is deposited by a well-established process known as low pressure chemical vapor deposition after carbon nanotubes 112 are grown, as illustrated in FIG. 4D.

Supporting silicon wafer 100 is then etched anisotropically to produce a small patch of free standing silicon nitride membranes that contain nanotube templates oriented perpendicular to the membrane surface of silicon nitride. Silicon dioxide can be used instead of silicon nitride because chemical vapor deposition of silicon dioxide is also a well-established technique. Finally, carbon nanotube 112 is removed through oxidative combustion at high temperature to result in the structure shown in FIG. 3E. The density of the nanopores within the membrane can be controlled by the density of the seeding of iron particles. At a very low seeding density, membranes containing single nanopore may be produced although the yield of these membranes may be low.

Figure 5A:
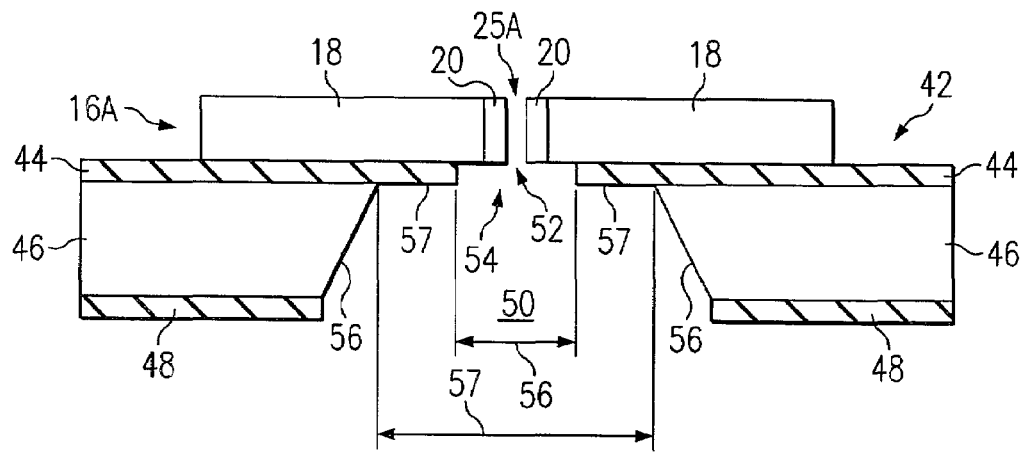
FIG. 5A illustrates an elevational view of a nanopore membrane assembly utilizing the nanopore membrane of FIG. 2A according to the teachings of the invention.

FIG. 5A is an elevational view of a nanopore membrane assembly 58 utilizing the single nanopore membrane 16A of FIG. 2A according to the teachings of the invention. Membrane 16A could be replaced with membrane 16B but membrane 16A is utilized as an example. Membrane 16A (or sections 40) may be applied to a support structure 42 for use as a particle detector or for other suitable purposes. In this particular embodiment, support structure 42 comprises silicon nitride ($Si_3N_4$) layers 44 and 48 separated by silicon regions 46. Silicon regions 46 form, in this embodiment, tapered region 50 having tapered edges 56. This tapered shape ensures that the portion of the free standing silicon nitride membrane 57 is minimized in its area. A reduced membrane area exposed to liquid solutions reduces measurement electronic noise. An approximately circular hole 54 is opened up using standard techniques of photolithography and reactive ion etching. Better operation is obtained if the diameter of the hole 54 is between five to twenty micrometers; however other dimensions may be used. In this example support-structure 42 is about 12.5 mm by 12.5 mm with a thickness of about 525 micrometers; however, any suitable size may be used.

Although a particular material for silicon nitride layers 42, 48 has been described, any material capable of supporting section 36 may be utilized. Further, although silicon was described as a particular material that may be used in region 46, other materials may also be used: these include organic polymers such as polystyrene and poly-dimethyl-siloxane or inorganic polymers such as glass, silica, and silicon nitride. In a particular embodiment, however, commercially available doped silicon is used for region 46 with a low doping density. Non-doped silicon is actually more desirable but is not as easily available. Section 40 may be accurately positioned over the hole 54 by moving it with a two-prong-fork fashioned from two sharp tungsten tips under an optical microscope. In this particular embodiment, the section 40 is floated on a thin film of water while being maneuvered to its target position. After the complete evaporation of the water film, the tungsten fork is removed, and the section 40 is affixed to the support structure by gentle heating at 40 degree Celsius for about 10 minutes. The resulting single nanopore membrane assembly 58 may be used in a Coulter counting method to count particles, such as the one described below in conjunction with FIGS. 5B through 5E, or in other applications, such as those involving flow of particles or other material through nanopore 25.

Figure 5B:
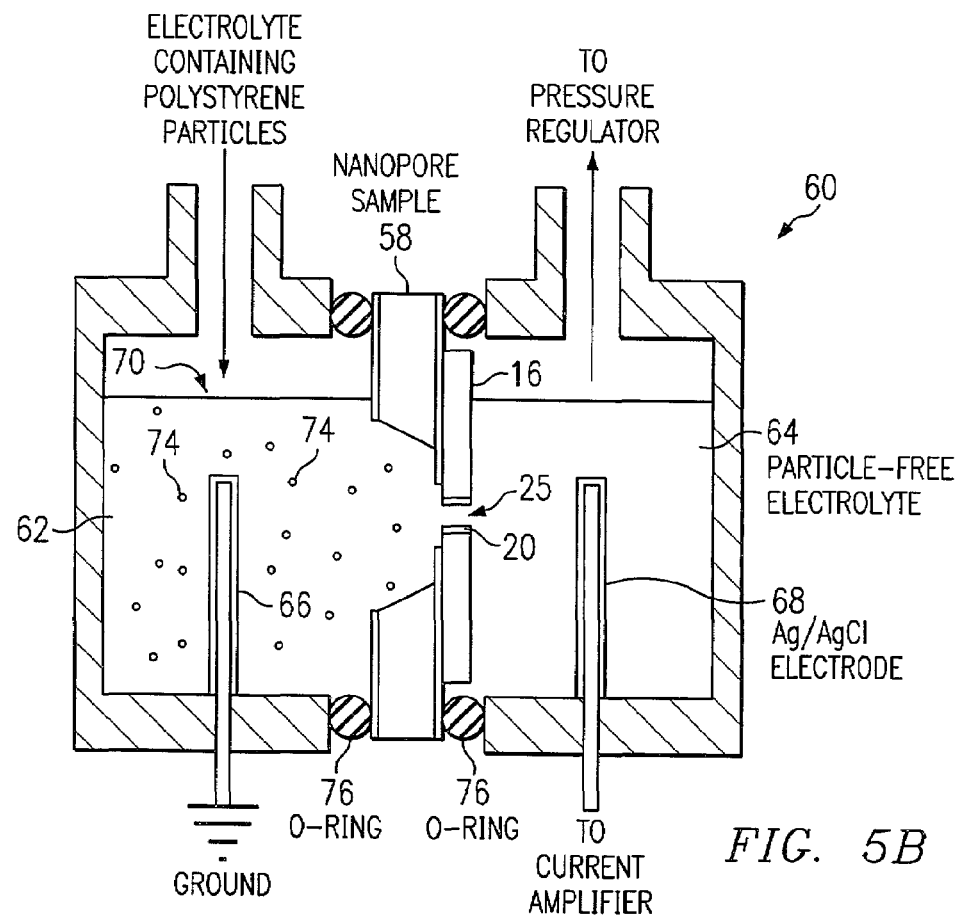
FIG. 5B illustrates an elevational view of a system for measuring transportation of nanoparticles utilizing the nanopore membrane assembly of FIG. 5A according to the teachings of the invention.

FIG. 5B is an elevational view of a measurement system 60 for measuring transportation of nanoparticles utilizing nanopore membrane 16 according to the teachings of the invention. If, over the entire surface of nanopore membranes 16, only one single nanopore connects the opposite sides of the membrane, then the single nanopore can serve as a detection zone as defined in a conventional Coulter particle counter. Coulter counters are based on measurements of changes in the ionic conductance of single pore, in this case, a single nanopore, caused by the particles to be detected as they move across the pore. Single nanopores 25 produced using nanotubes 10 are well-suited for this purpose because of their well-defined geometric as well as chemical structures.

Measurement cell 60 includes two chambers 62 and 64 separated by nanopore membrane assembly 58 and a set of O-rings 76. In this example, each chamber 62, 64 encloses a Ag/AgCl electrode 66, 68 and electrolyte solution 70, 72. Electrolyte solution 70, 72 may be, in this example, 0.1M KCl, 0.1% (w/v) Triton X-100 with a 10 mM pH 7 phosphate buffer; however, other solutions may also be used. These solutions may be filtered prior to use. Chamber 64 is connected to a water-filled barometer (not explicitly shown) for pressure control and readout. Chamber 62 is loaded with a plurality of probe particles 74. In this particular example, probe particles 74 are polystyrene probe particles; however, any particle for which detection is desired may be utilized. Solution 70 is an electrolyte solution such that flow of ions dissolved in the electrolyte from chamber 62 to chamber 64 or from chamber 64 to chamber 62 may be induced by an electric potential difference between electrode 66 and electrode 68.

Figure 5C:
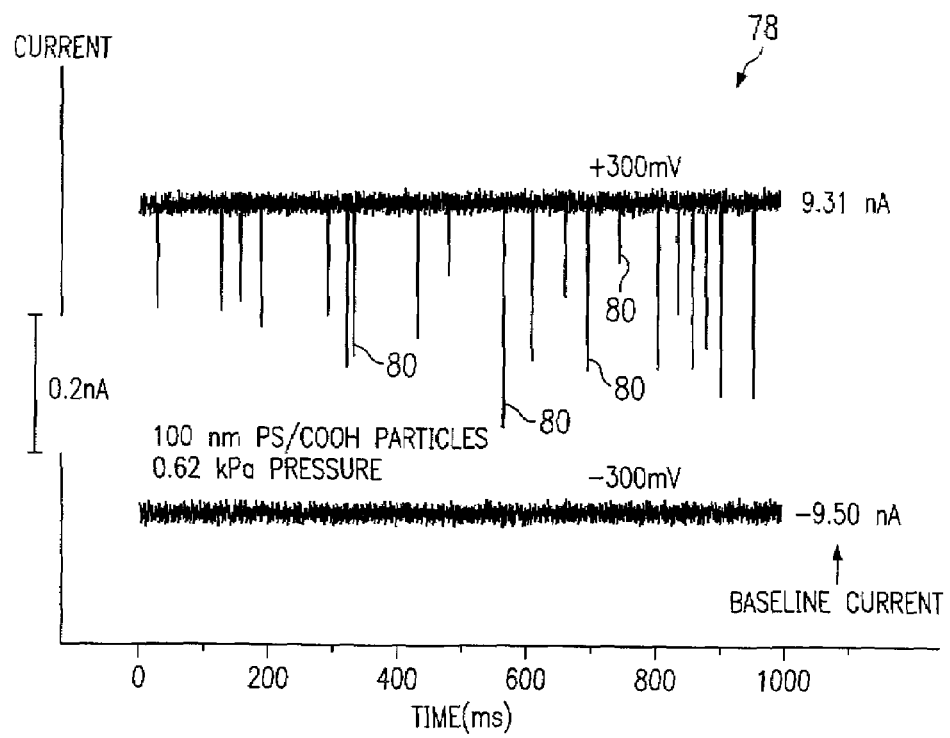
FIG. 5C is a graph showing movement of particles through the nanopore membrane assembly of FIG. 5 according to the teachings of the invention.

In operation, flow of probe particles 74 and charged ions is induced through nanopore 25. Such flow may be detected according to conventional techniques, such as measuring a resulting ionic current through nanopore 25 caused by movement of the ions. When a particle 74 flows through nanopore 25, this disrupts the flow of ions in a rapid reduction, or spike, in the measured current through nanopore 25. Such spikes are illustrated in FIG. 5C. By counting the spikes in the measured current flow, the movement of particles from chamber 62 to chamber 64 may be detected and analyzed.

The above procedure is based on the Coulter counting principle. A Coulter counter detects a probe particle by monitoring the current pulse induced by the probe as it moves across a single pore. In the absence of the probe, the baseline ionic current, $i_p$, is $$i_p = \frac{\kappa \pi d_p^2 \Delta E_p}{4(l_p + 0.8 d_p)} \quad (1)$$

where $\Delta E_p$, is the voltage across the membrane; $\kappa$ is the electrolyte conductivity; $d_p$ is the pore diameter; and $l_p$ is the pore length. The current pulse, $\Delta i_p$, induced by the probe is $$\frac{\Delta i_p}{i_p} = S(d_P, d_s) \frac{d_S^3}{(l_P + 0.8 d_P) d_P^2} \quad (2)$$

where $d_s$ is the diameter of the probe sphere, and $S(d_p, d_s)$ is a correcting factor that depends on $d_p$ and $d_s$.

Coulter counting can provide a wide variety of information about mass-transport kinetics. For example, the size of every probe particle transported through the pore can be calculated using Eq. 2, and the velocity of the probe can be calculated from the pulse width. In addition, the average probe velocity, $V_S$, is related to the particle flux, $J_S$, by $$v_S = \frac{4 J_S}{\pi c_S d_P^2} \quad (3)$$

where $c_S$ is the probe sphere concentration. The observed velocity, $v_S$, may be broken down into four terms, which correspond to contributions from hydrodynamic transport, electrophoretic and electroosmotic transport, and diffusion:

$$v_S = \frac{d_P^2}{32 \eta l_P} \Delta P + \frac{\mu_S}{l_P} \Delta E_M - \frac{\varepsilon \zeta_P}{4 \pi \eta l_P} \Delta E_M + \frac{D_S}{c_S l_P} \Delta c_S \quad (4)$$

where $\eta$ and $\in$ are medium's viscosity and dielectric constant, respectively; $\mu_s$ and $D_s$ are probe sphere's electrophoretic mobility and diffusion coefficient, respectively; and $\zeta_p$ is the zeta potential of the pore surface.

Polystyrene spheres of 100 nanometer diameter or less can be detected by a nanotube-based Coulter counter, as shown below. Other types of particles in the size range of less than a 100 nanometers, such as virus particles can also be detected. As the diameter of nanotube 10 is reduced further, that is, approaching molecular dimension, large polymeric molecules can also be detected. These polymeric molecules include man-made polymer such as poly-ethyleneglycol and dendrimers or natural polymers such as DNA's, proteins, polysaccharides and antibodies.

Besides their use as Coulter counters, nanopores 25A and 25B formed using nanotubes 10 can be used in other applications where fluidic mass transport through nanopores is required. Fluidic transport of gaseous or liquid materials through nanopores has many potential applications. Such transport may be realized by applying the following and other types of driving forces across a nanopore: 1) a pressure gradient, 2) an electric field gradient, and 3) a concentration gradient.

FIG. 5C is a graph showing movement of particles through the single nanopore membrane assembly 58 of FIGS. 5A and 5B according to the teachings of the invention. As illustrated, a baseline current level, represented by reference numeral 78, indicates a relatively constant electrical current arising from the flow of ions in electrolytes from chamber 62 to chamber 64. However, at various times a spike 80 indicates a sudden drop in current flow. This occurs when a particle 74 flows through nanopore 25. As described above, the flow of the particle through nanopore 25 constricts the flow of ions, resulting in a lower measured current. Thus, this procedure allows the detection and the identification of particles flowing from one region to another, which has many practical applications. Other information regarding the flow and size of particles 74 may be obtained according to equations 1 through 4, as described above.

Figure 5D:
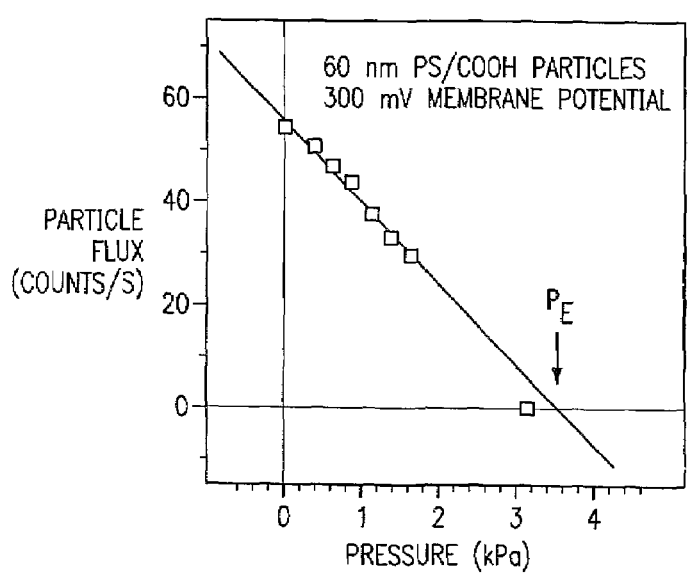
FIGS. 5D and 5E are graphs showing experimental data generated by the nanopore membrane assembly of FIG. 5B.
Figure 5E:
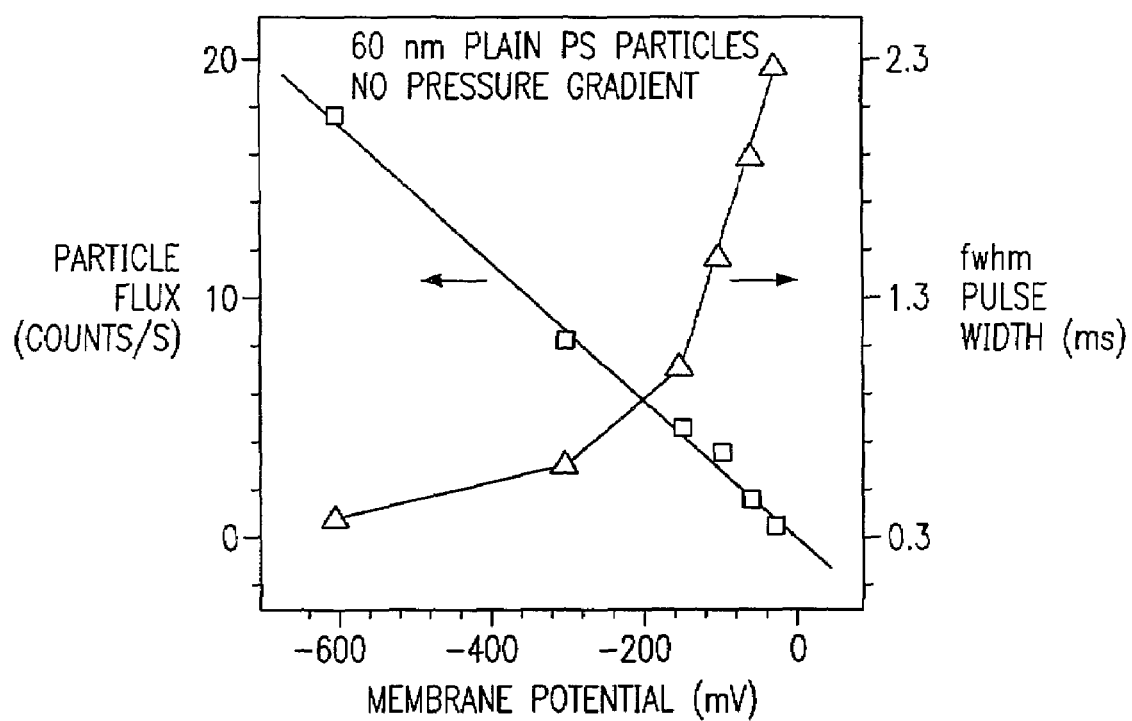

FIGS. 5D and 5E show that, in accordance with Eq. 4, the transport rate of particles measured in an example implementation of the system of FIG. 5B utilizing nanopore membrane assembly 58 varies linearly with respect to the pressure gradient or the electric field gradient. In the above example, the slopes of the first and second terms in Eq. 4 for hydrodynamic and electrophoretic transport can be measured quantitatively, and the results agree approximately with values calculated according to Eq. 4. The first and the third terms of Eq. 4 are not completely independent of one another: for example, a hydrodynamic flow across a charged pore will induce a streaming potential. The streaming potential measurements indicate that the inner surface of the carbon nanopore is essentially neutral ($-1$ mV$<\zeta_p<0$ mV); thus, the electroosmotic transport plays a less dominant role compared to the hydrodynamic and electrophoretic components. In this example, diffusion also plays a less dominant role, and in fact it is probably the slowest among the aforementioned modes of transport.

Figure 6:
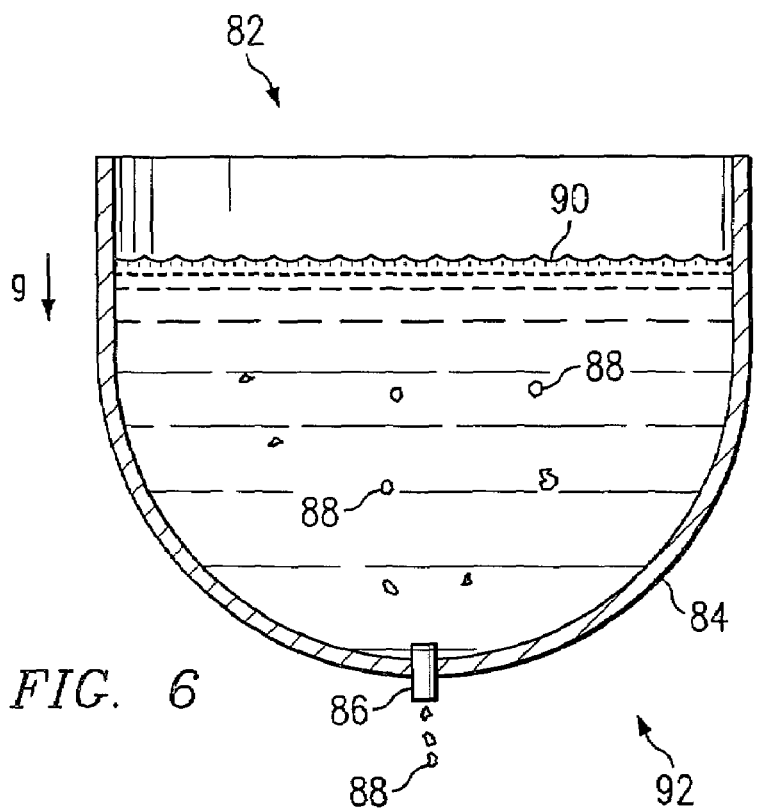
FIG. 6 is a perspective drawing showing a system for delivering material to a desired location that includes a nanotube holder with a nanotube embedded therein.

FIG. 6 is a schematic drawing showing a system, or assembly 82, for delivering material to a desired location that includes a nanotube holder 84 and a portion of a nanotube 86 embedded therein. Assembly 82 may be filled with a material 90, such as liquid or gas, containing a plurality of particles 88, or no particles 88. The desired location may be filled with a material 92, such as liquid or gas, or filled with nothing, that is, vacuum.

According to the teachings of the invention, particles 88 (or alternatively material 90) may be transported from nanotube holder 84 to a desired region outside nanotube holder 84 through nanotube portion 86. In this example, gravity provides the force pushing particles 88 through nanotube 86. Other examples of forces that may be used to force particles 88 (or material 90) through nanotube 86 may arise from a pressure gradient, an electric field gradient, a concentration gradient, or a centrifugal force field; however, other types of forces may also be used. In this sense, assembly 82 with nanotube portion 86 may act as a pipet, but for extremely small particles. Nanotube holder 84 may be any suitable structure that may contain a substance to be transported to a desired area and that may be formed around a nanotube portion 86. Examples and materials for support structure 84 include organic polymers such as polystyrene and poly-dimethyl-siloxane or inorganic polymers such as glass, silica, and silicon nitride; however, others may also be utilized. Assembly 82 may be used to transport a plurality of particles such as biological particles and non-biological particles, as described above.

Although several embodiments have been illustrated and described in detail, it will be understood that various substitutions and alterations can be made therein without departing from the teachings of the present invention. For example, although numerous other changes, substitutions, variations, alterations, and modifications may be ascertained by those skilled in the art and it is intended that the present invention encompass all such changes, substitutions, variations, alterations, and modifications as falling within the spirit and scope of the appended claims. Moreover, the present invention is not intended to be limited in any way by any statement in the specification that is not otherwise reflected in the appended claims.

What is claimed is:

1. An apparatus comprising:
   a membrane;
   a nanotube embedded within the membrane and providing a conduit through the membrane, the ends of the nanotube being flush with respective surfaces of the membrane; and
   wherein the nanotube is a carbon nanotube.

2. A method of forming a membrane having a small hole disposed therein comprising:
   surrounding at least a portion of a nanotube with a material; and
   sectioning the material and the nanotube to produce the membrane having the small hole disposed therein.

3. The method of claim 2, wherein surrounding at least a portion of the nanotube with a material comprises surrounding at least a portion of the nanotube with a polymer precursor in liquid form and then solidifying the polymer.

4. The method of claim 2, wherein sectioning the material comprising slicing a thin membrane off the material with a knife.

5. The method of claim 2, and further comprising removing the nanotube from the sectioned material.

6. A method of forming a membrane having a small hole disposed therein comprising:
   surrounding at least a portion of a nanotube with a liquid or gaseous material;
   allowing the liquid or gaseous material to solidify around the nanotube; and
   removing by chemical oxidation the at least a portion of the nanotube from the solidified material, leaving the membrane having the small hole disposed therein.

7. The method of claim 6, wherein surrounding the at least a portion of a nanotube with a liquid or gaseous material and allowing the liquid or gaseous material to solidify around the nanotube comprises depositing an inorganic solid around the nanotube.

8. The method of claim 7 wherein an inorganic solid comprises silicon nitride.

9. The method of claim 7 wherein an inorganic solid comprises silicon dioxide.

10. The method of claim 7, wherein depositing an inorganic solid comprises depositing the solid by chemical vapor deposition.

11. A method for detecting particles comprising:
    providing a membrane having a portion of a nanotube disposed therein that provides a conduit through the membrane;
    allowing the particles to pass through the membrane through the conduit of the nanotube;
    detecting the passage of the particles through the conduit of the nanotube; and
    wherein allowing the particles to pass through the membrane through the conduit of the nanotube comprises applying a pressure differential across the membrane.

12. A method for delivering a liquid material to a desired location comprising:
    providing a nanotube holder between the liquid material and the desired location, the nanotube holder having a portion of a nanotube disposed therein that provides a conduit through the holder; and
    forcing the liquid material through the holder to the desired location by forcing the liquid material through the conduit of the nanotube.

13. The method of claim 12, wherein forcing the liquid material comprises applying a concentration gradient across the conduit of the nanotube.

14. The method of claim 12, wherein forcing the liquid material comprises applying a pressure differential across the conduit of the nanotube.

15. The method of claim 12, wherein forcing the liquid material through the holder comprises applying an electric field across the conduit of the nanotube.

16. The method of claim 12, wherein forcing the liquid material through the holder comprises placing the nanotube holder in a centrifugal force field.

17. The method of claim 12, wherein the nanotube holder comprises a membrane.

18. The method of claim 17, wherein the membrane comprises a polymer.

19. The method of claim 17, wherein the membrane comprises an inorganic solid.

20. The method of claim 17, wherein the membrane comprises glass.

21. The method of claim 17, wherein the membrane comprises a glass reservoir.

22. The method of claim 12, wherein the liquid material comprises a plurality of microscopic particles.

23. The method of claim 12, wherein the desired location comprises a liquid medium.

24. The method of claim 12, wherein the desired location comprises a gas medium.

25. The method of claim 12, wherein the desired location comprises a vacuum of less than one atmosphere of pressure.

26. A method for delivering material to a desired location comprising:
- providing a nanotube holder between the material and the desired location, the nanotube holder having a portion of a nanotube disposed therein that provides a conduit through the holder;
- applying a pressure differential across the conduit of the nanotube to force the material through the holder to the desired location by forcing the material through the conduit of the nanotube; and
- wherein the material comprises a liquid.

* * * * *